United States Patent [19]

Baierl

[11] 4,071,398

[45] Jan. 31, 1978

[54] CHEMICAL CONCENTRATION BY SEQUENTIAL ACTIVATED CARBON ADSORPTION AND FRACTIONATION

[75] Inventor: Kenneth W. Baierl, Appleton, Wis.

[73] Assignee: Flambeau Paper Company, Park Falls, Wis.

[21] Appl. No.: 733,306

[22] Filed: Oct. 18, 1976

Related U.S. Application Data

[63] Continuation of Ser. No. 587,850, June 18, 1975, abandoned.

[51] Int. Cl.$^2$ .............................................. D21C 11/06
[52] U.S. Cl. ........................................ 162/15; 162/16; 203/41; 203/74; 203/78; 203/98; 203/DIG. 11; 210/26; 210/34; 210/40
[58] Field of Search .............. 162/14, 15, 16; 210/26, 210/40, 34; 203/78, 98, 41, 74, DIG. 11

[56] References Cited

U.S. PATENT DOCUMENTS

| 3,448,042 | 6/1969 | Mattia et al. | 210/40 |
| 3,499,935 | 3/1970 | King | 203/91 |

OTHER PUBLICATIONS

Baierl et al. "Tapoi" vol. 56, No. 7, July, 1973, pp. 58-61.

Primary Examiner—S. Leon Bashore
Assistant Examiner—William F. Smith
Attorney, Agent, or Firm—Schmidt, Johnson, Hovey & Williams

[57] ABSTRACT

A continuous, low cost method of concentrating dilute streams containing fractions of adsorbable chemicals is disclosed which minimizes heat consumption and provides highly concentrated supplies of valuable chemicals which are suitable for reuse or sale without substantial further processing. The methods hereof are particularly adapted for concentrating waste condensates derived from pulp-making operations such as the Kraft or sulfite processes, but in general are also applicable for treating a wide variety of dilute organic or inorganic adsorbable chemicals. The invention involves initially adsorbing and concentrating a chemical fraction from the dilute stream followed by desorption and recycling of the adsorbed materials to further concentrate the same, whereupon the desorbed chemicals are directed to a second concentration zone and concentrated therein; at this point the partially concentrated steam is diverted back to the adsorption zone for further adsorption and concentration simultaneously with the dilute stream initially passing therethrough, while concentration continues in the second zone to yield a final product having a concentration on the order of 90% by weight or better. In preferred forms only a single fractionating column is employed in the second concentration stage which minimizes capital costs and reduces steam consumption, while recycling back to the adsorption zone permits continuous operation of one fractionation column doing the work of two or more columns. Thus, dual use of the single fractionator column in both intermediate and final concentration steps allows continuous operations with equipment heretofore used only in batch-type operations.

12 Claims, 4 Drawing Figures

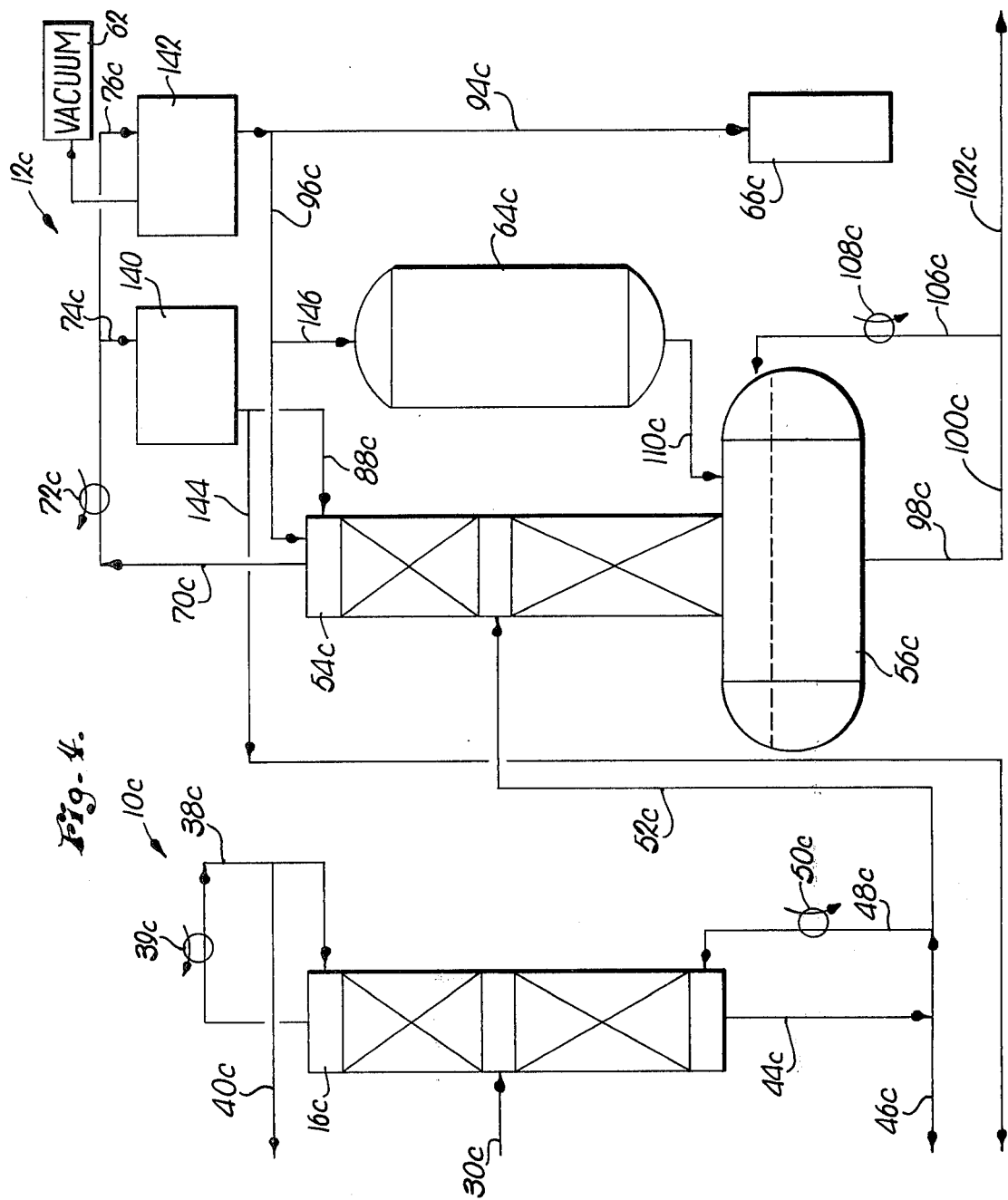

CHEMICAL CONCENTRATION BY SEQUENTIAL ACTIVATED CARBON ADSORPTION AND FRACTIONATION

This is a continuation, of application Ser. no. 587,850, filed on 6/18/75 now abandoned.

This invention is concerned with the efficient and economical treatment of many types of waste liquors containing valuable chemical constituents, and especially those derived from pulp-making processes, for example the well-known sulfite and Kraft processes. More particularly, it is concerned with such a treating method which involves sequential adsorption and fractionation and is characterized by extremely low steam consumption and equipment costs notwithstanding the fact that the recovered products are of high purity and suitable for immediate sale or reuse. In its broader aspects, the invention is not restricted to pulp-making processes, but rather can be employed as an adjunct to a variety of textile, chemical and petrochemcial processes in common use today. For example, a wide variety of sugars, alcohols, aldehydes, acids, condensates, dye production effluents and organic chemicals such as aldehydes, phenols, cymenes, saturated oils, high molecular weight organic impurities and taste and odor components can be concentrated and recovered by the methods hereof.

Paper mills and other chemical processing plants have for a very long time engaged in the practice of simply dumping their process waste effluent streams into the nearest river or waterway. This not only presents a real threat to the ecology, but in many instances the discarded materials would have substantial commercial value if they could be concentrated and treated for resale and reuse at a practical cost. In the latter connection, constantly increasing equipment, fuel and operating costs have in many cases made conventional recovery techniques extremely uneconomical and therefore impractical.

At the same time, increasingly stringent governmental pollution regulations have caused concern. In particular, newly promulgated environmental protection standards have drastically reduced the allowable amount of pollutant which may be discharged into rivers or the like. As a consequence of these factors, many chemical processing plants have been forced to add expensive pollution abatement equipment in order to meet environmental regulations, which of course also has the effect of increasing operational costs because of increased energy consumption.

In the papermaking industry, sulfite pulp-making condensates contain minor proportions of potentially valuable chemicals such as acetic acid, methanol, furfural and sulfur dioxide. These waste streams are extremely dilute, i.e., in many cases are 99% or more water, and this fact of course materially increases the difficulty of extracting these chemical constituents at a practical costs. For example, although it would be theoretically possible to fractionally distill these waste streams to separate out the acetic acid and furfural components for example, as a practical matter the steam consumption attendant to such a distillation procedure would drive the concentration and recovery costs far beyond the commercial value of the recovered chemicals. Hence, there has heretofore been no really successful answer to the problem of concentrating and recovering valuable chemical constituents from extremely dilute streams thereof at a relatively low cost in terms of equipment needs and energy consumption.

It is therefore the most important object of the present invention to provide a simplified, continuous, low cost method of treating dilute streams containing valuable adsorbable chemical fractions in a manner to produce and recover concentrated supplies of such chemicals, notwithstanding minimization of the equipment needs and processing costs attendant to such a method.

Another object of the invention is to provide a continuous, sequential adsorption-fractionation method wherein dilute streams of chemicals, e.g., waste condensates derived from the chemical, petrochemical or textile industries, or the Kraft and sulfite pulp-making processes, are first subjected to an adsorption treatment in order to partially concentrate the same whereupon the adsorbed chemical fraction is desorbed and passed to a secondary concentration zone which preferably includes a single fractionation column; the desorbed products are further concentrated in the secondary concentration zone to a desired level, at which point the delivery of the partially concentrated stream is stopped and the latter is redirected back to the adsorption zone for further reconcentration therein. At the same time, the concentration of the chemicals within the secondary zone is continued in order to finally concentrate these chemicals to a desired level which may be on the order of 99% or better so that equipment normally usable in batch-type operations can be employed on a continuous basis.

Figure 1:
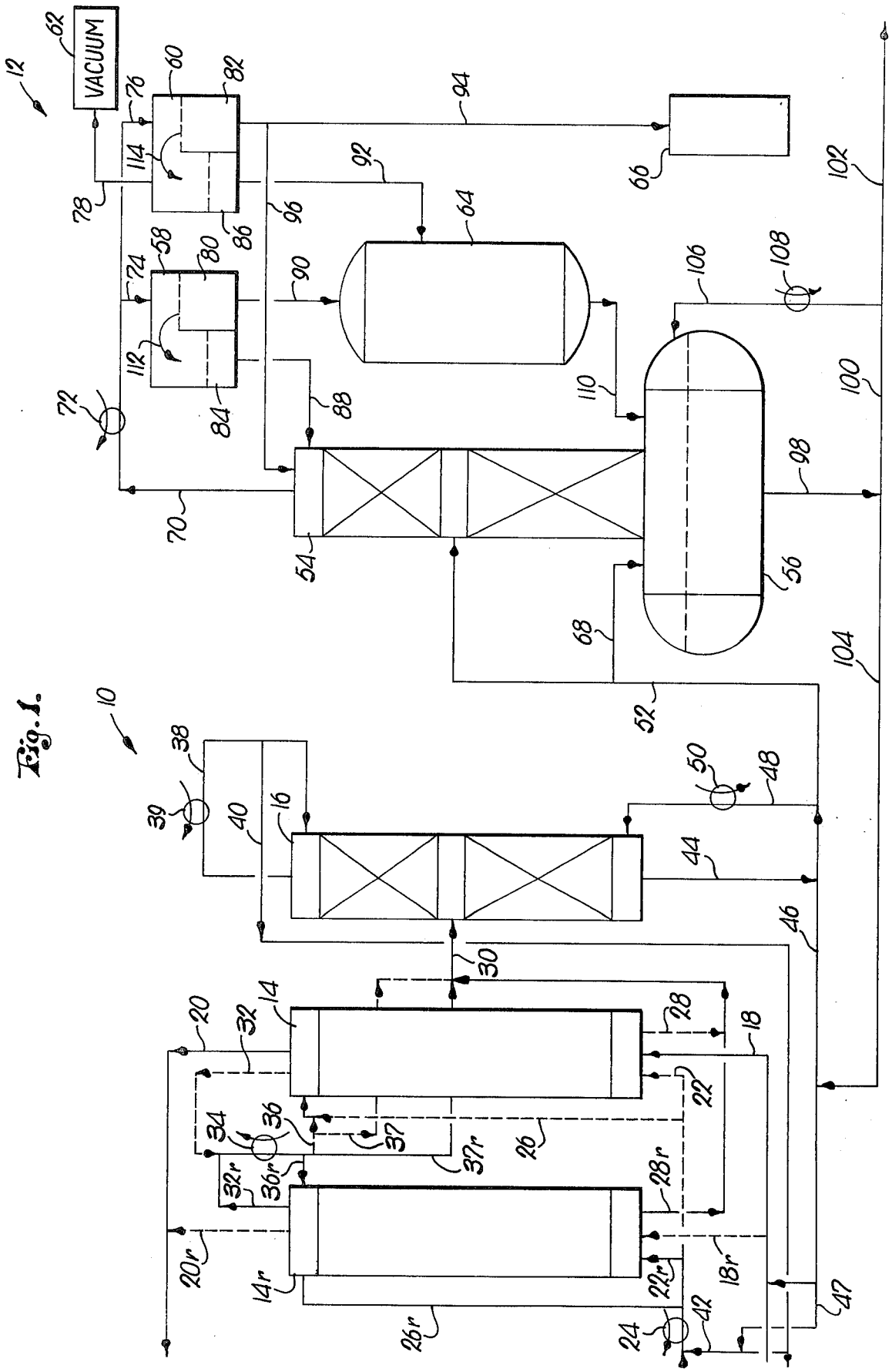
FIG. 1 is a schematic representation of apparatus in accordance with the invention which is adapted for the production of concentrated supplies of furfural from a dilute supply of sulfite pulp-making condensate using alcohol as the carbon chemical desorbing agent.
Figure 3:
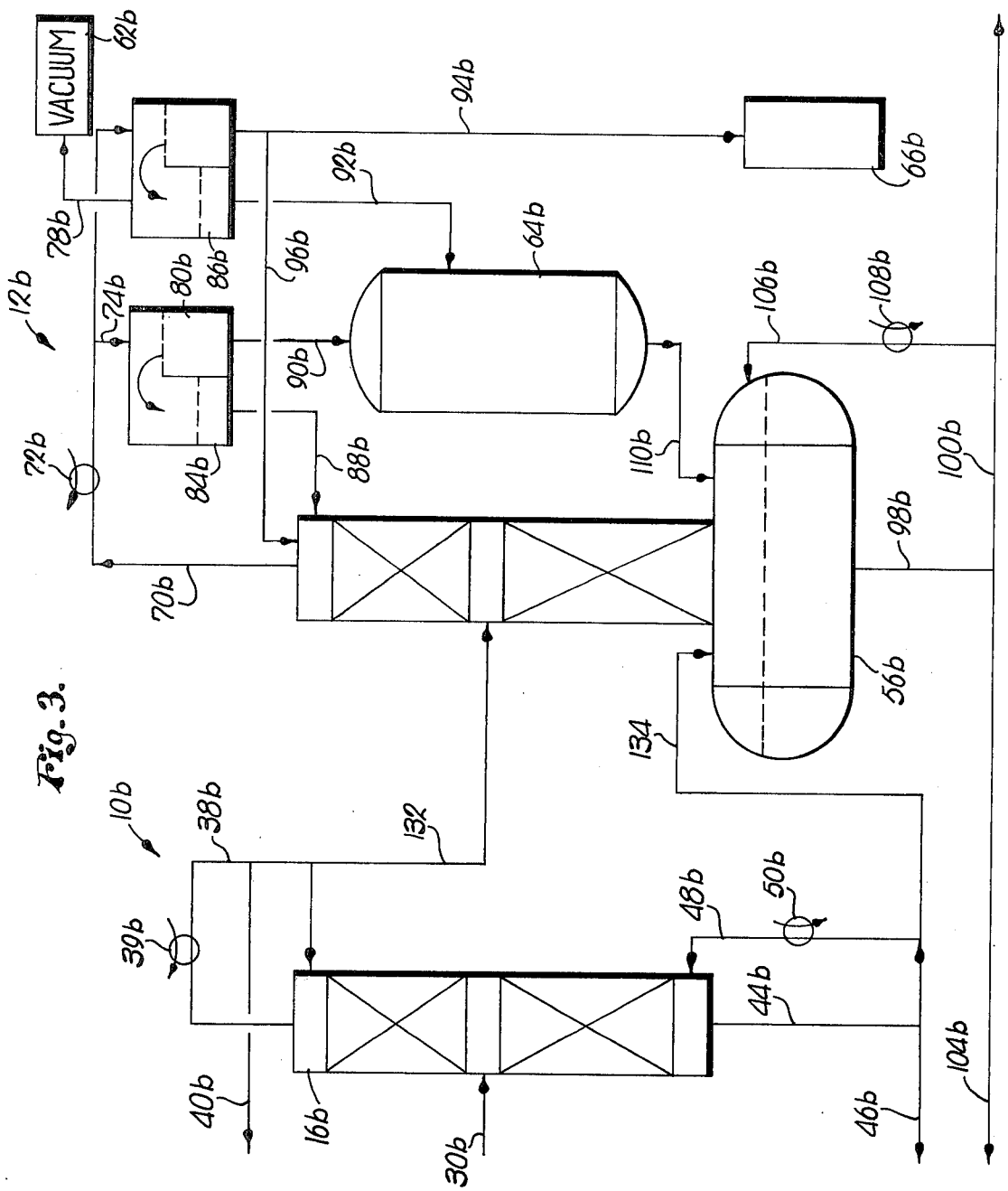

FIG. 3 is a fragmentary, schematic representation similar to that depicted in FIG. 1 but further modified using steam as the carbon chemical desorbing agent for the production of concentrated furfural; and FIG. 4 is a fragmentary, schematic representation of apparatus in accordance with the invention which is adapted for the production of acetic acid from sulfite pulp-making condensates using alcohol as the carbon chemical desorbing agent.

In its broadest aspects, the present invention pertains to a sequential adsorption-concentration process which is operable to efficiently and economically concentrate dilute supplies of a wide variety of chemicals to yield concentrated supplies of the same. Moreover, the process is especially adapted for continuous operations notwithstanding the fact that the equipment requirements are held to a minimum and operating costs such as stream consumption are drastically reduced.

The process includes first directing the dilute stream of chemicals to a first concentration zone which contains an adsorption media, preferably activated carbon. The desired chemicals contained in the dilute supplies thereof are then adsorbed onto the adsorption media whereupon the clarified feed can be disposed of or reused. In this connection the first concentration zone preferably contains at least two parallel-connected activated carbon column which are interrelated such that when one column is in the adsorption stage, the remaining column is being regenerated. In order to facilitate continuous operations, the columns are preferably sized to handle the dilute feed and recycle for a relatively long time, e.g., for a period of about 120 hours for dilute feed containing furfural.

Subsequent to the adsorption step the chemicals are desorbed by contacting the adsorption media with a regenerating agent and a partially concentrated stream of the desired chemical is produced which is more concentrated than the initial dilute stream. In the case of treating sulfite waste liquors, the regenerating agent is preferably selected from the group consisting of the lower alcohols, acetone and moisture, or most preferably methanol, ethanol and steam. For example, if the adsorption column is sized and adapted for adsorbing the furfural component of sulfite condensates, regeneration with methanol or the like will produce a concentrated stream of furfural which is then further treated in the secondary concentration and recovlery stage to yield a 90% by weight or better concentrated product.

In certain forms of the invention, the next step involves concentrating the desorbed products to yield a further concentrated stream thereof. In preferred form this concentration is effected by fractionally distilling the chemicals in a conventional two-stage steam fed fractionator. However, in continuous operations using a solvent more volatile than water (such as methanol) this initial, first stage fractionation step does not serve to appreciably concentrate the desorbed chemicals.

The next stage in operation in accordance with the present invention involves directing the partially concentrated streams to a second concentration zone and concentrating the same to a desired level, whereupon the delivery of additional materials to the second zone is terminated and the stream is recycled back to the adsorption zone for readsorption of the desired chemical therein along with adsorption of such chemical from the initial, dilute stream. At the same time, concentration in the second zone is continued in order to produce a final, highly concentrated product. After recovery of such final product delivery of fresh material to the second zone is recommenced, and the process continued. Thus, by virtue of the adsorption zone, it is possible to provide a continuously running process using equipment heretofore used in conjunction with batch-type operations.

In one preferred form, the second concentration zone comprises a steam-fired fractionator along with apparatus for collecting the overhead and underflow from the fractionator and temporarily holding that portion thereof containing the desired chemical. When the holding zone is filled with the chemical at a desired intermediate concentration, delivery of the partially concentrated stream to the second concentration zone is stopped and this stream is redirected back to the adsorption zone for passage therethrough simultaneously with the dilute stream. The holding zone is thereafter emptied and the contents thereof are delivered to the fractionator whereupon final concentration operations are started and continued until a final product is recovered. Thus, a single fractionator serves the dual function of intially concentrating the chemical stream to an intermediate level, and thereafter reconcentrating the stream to a highly concentrated level.

In other preferred embodiments, single or multiple decanting apparatus is provided in the secondary concentration stage for the purpose of facilitating separation and ultimate concentration of the desired chemicals. Moreover, a vacuum source is preferably provided in such embodiments for the purpose of permitting vacuum-assisted distillation of the chemical stream in the final concentration step.

The following discussion involves a description of the apparatus and operation of each of the embodiments depicted in the drawings, along with examples demonstrating the use thereof in producing concentrated supplies of valuable chemicals from dilute pulp-making condensates. It is to be clearly understood however, that the following discussion and examples are merely illustrative of the invention but in no way constitutes limitations thereon.

FIG. 1 EMBODIMENT

This embodiment broadly includes an adsorption fractionation stage 10 and a series-coupled furfural recovery stage 12. The overall apparatus is especially designed for the continuous recovery of concentrated supplies of furfural from sulfite pulp-making waste condensates. In particular, this embodiment of the invention utilizes sequential adsorption, desorption, recycling and distillation to economically produce approximately 99% by weight furfural product from an initially 0.1% by weight furfural pulp mill effluent. In more detail, stage 10 includes a pair of serially interconnected carbon columns 14 and 14r along with a two-stage fractionation column 16. As will be explained more fully below, the respective columns 14 and 14r are designed to alternate between adsorption and regeneration operations, but for purposes of the present discussion it will be assumed that column 14 and related equipment serves as the adsorption column, while column 14r and related equipment is provided for regeneration. In any event, an incoming product line 18 is connected to the bottom of column 14 for the purpose of directing waste condensates to the latter, and has a tap-off 18r therefrom leading to the bottom of column 14r. In the drawing, the dotted line would be closed during adsorption with column 14 and simultaneous regeneration with column 14r. Clarified feed lines 20 and 20r are connected to the top of the respective columns for conveying the effluent from the column for reuse or further purification. Regeneration lines 22 and 22r are also connected to the bottom of the respective columns and pass through a steam-fired reboiler 24 which serves to vaporize the regeneration agent (such as alcohol or steam) prior to entry thereof into the carbon column. Respective lines 26 and 26r are connected to the regeneration lines associated with each column and extend to the top of the latter for the optional delivery of regeneration media thereto to provide a reflux within the carbon column.

Product recovery lines 28 and 28r are connected to the bottom of each carbon column and extend to a line 30 which is in turn connected to center of two-stage fractionation column 16. Upper product recovery lines 32 and 32r are attached to the top of the respective carbon columns and both of these lines pass through a cold water heat exchanger 34 and are ultimately connected to line 30 as illustrated. Recycle lines 36 and 36r are connected to the line extending between heat exchanger 34 and line 30 and respectively lead back to the top of column 14r and column 14. In the latter case, lines 36 and 38r are connected to bypass lines 37 and 37r which are connected to line 30. Line 36 is connected to recycle line 26 as shown.

Fractionation column 16 includes an upper overhead loop line 38 having a cold water heat exchanger 39 interposed therein for the purpose of recycling condensed fractionator overhead vapors. In this regard, a line 40 is connected to loop line 38 for the purpose of removing the condensed overhead vapors from column 16 as desired. Line 40 may be employed for returning alcohol to the system via line 42 or optionally to a storage tank therefore (not shown). A line 44 is connected to the bottom of column 16 and also to lines 46 and 48 respectively. In this regard, line 46 provides a recycle back to the carbon column 14 and 14r via lines 18 and 18r, while line 48 provides a loop recycle back to the bottom of column 16 and has a steam-fired reboiler 50 interposed therein.

A line 52 is connected to the bottom of line 44 from fractionator 16 and extends to fractionation column 54 forming a part of second stage 12. In particular, stage 12 includes column 54 coupled to a lower receiving vessel 56 along with a pair of decanters 58 and 60, a vacuum source 62, a holding tank 64 and conventional drum loading apparatus 66.

As illustrated, line 52 is connected to the midportion of fractionation column 54 and has a recycle line 68 connected thereto and leading directly to tank 56. An overhead line 70 is connected to the top of column 54 and has a cold water heat exchanger 72 interposed therein. Tap-off lines 74 and 76 are respectively connected to decanters 58 and 60, with the latter decanter being connected to vacuum source 62 by way of line 78.

Each of the decanters 58 and 60 is of conventional construction and includes a first holding section 80 and 82 respectively, as well as partitioned overflow sections 84 and 86. A recycle line 88 is connected to overflow section 84 of decanter 58 and extends back to the top of fractionation column 54. In addition, a product line 90 is connected between section 80 of decanter 58 and holding tank 64. Finally decanter 60 includes a delivery line 92 between the overflow section 86 thereof and tank 64, as well as final product line 94 extending between section 82 thereof and drum loading structure 66. Line 94 also has a recycle line 96 connected thereto which leads back to the top of column 54.

As illustrated, tank 56 is situated below column 54 and receives the fractionated bottoms therefrom. This tank also has a line 98 connected thereto which is ultimately attached to line 100. The latter includes a portion 102 for conveying water and polymerized material away from the system, and a portion 104 loading back to stage 10 and being connected to line 46 thereof. In addition, a line 106 is connected to line 100 and finds a loop recycle back to tank 56. Line 106 also includes a steam-fired reboiler 108 for providing indirect steam to column 54. Finally, a line 110 is connected between tanks 64 and 56 as illustrated for conveying chemical streams from the former to the latter.

In operation, a waste condensate stream including furfural is passed through line 18 to the bottom of activated carbon adsorption column 14 for upward travel therethrough. During adsorption operations within column 14, column 14r will be simultaneously undergoing regeneration, and consequently line 18r, and all others illustrated by dotted lines, will be closed. This has the effect of adsorbing the furfural content of the stream onto the activated carbon, with a clarified feed leaving the system via line 20. Once the carbon within column 14 has reached its adsorption limit for furfural, such carbon must be regenerated and the furfural recovered. In this embodiment column 14 (and 14r) are sized to handle the feed and recycle of furfural-containing stream for a period of about 120 hours.

Turning now to the regeneration step in connection with column 14r, vaporized methanol or other regenerating agent is fed into column 14r via lines 22r, 26r. In this connection reboiler 24 serves to vaporize the methanol in these lines using indirect steam as a heating media. Line 26 can be employed as needed to give an effective up-down refluxing action of the methanol within column 14r in order to more effectively purge the latter of adsorbed furfural. During this regeneration cycle, crude furfural is passed through lines 28r, 30 to column 16, with the methanol overhead passing out via line 32r, being condensed in condenser 34, and optionally being recycled via line 36r to the top of column 14r to provide a reflux of the condensed overhead alcohol vapors. Line 32r also extends and is the source for line 30 leading to fractionation column 16 for feeding a methanol containing stream to the latter.

The furfural-methanol mixture entering column 16 through line 30 is fractionally distilled in the conventional manner by virtue of the indirect steam provided by steam-fired reboiler 50 interposed in recycle line 48. During the initial stages of fractionation the liquid from bottom line 44 is returned to carbon column 14 via lines 46 and 18, with a fraction thereof being recycled through line 48 as explained. As the furfural concentration in bottom line 44 increases to a desired level however, this material is sent via line 52 to second stage 12. Also during this initial fractionation process the overhead methanol vapors are selectively recycled through loop line 38 and condenser 39 until a relatively pure methanol product is being produced, at which point the overhead is directed via line 40 for reuse or storage.

The furfural crude product in line 52 contains considerably more concentrated furfural than that of the dilute stream entering first stage 10. For example, in the case of sulfite waste liquor feed having a furfural concentration of about 0.07% by weight, the first stage is operable to concentrate the furfural to approximately 22% by weight. In any event, as the furfural crude passes down column 54 into vessel 56 it is recycled via lines 98, 100 and 106 and passes through reboiler 108 whereupon it is vaporized by using indirect steam. This vapor passes up through vessel 56 and column 54 in order to strip the furfural out of the incoming feed. This has the result of forcing furfural vapor out of the top of column 54 through line 70. On the other hand, the aqueous bottoms include polymerized material which may either be discarded or separated during later purification steps. These bottoms in tank 56 can selectively be returned to column 14 or 16 through line 104 or be removed from the system entirely via line 102.

The excess steam and furfural vapor leaving column 54 through line 70 are condensed in heat exchanger 72 and are directed through line 74 to decanter 58. As shown, line 74 initially directs the condensate into section 80 of decanter 58 whereupon it travels via line 90 into collection tank 64. In this regard, since the furfural in the vapor exceeds its solubility in the condensate and is heavier than the saturated solution of furfural in water, the furfural collects as a saturated solution of water in furfural in tank 64. As it collects, the saturated solution of furfural in water fills tank 64 and section 80 of decanter 58 and overflows as shown by arrow 112 into section 84 of decanter 58. At this point, it travels via recycle line 88 back to the top of column 54 for further concentration thereof. This process is continued until a furfural crude of desired concentration fills up in tank 64. In practice, approximately a 92% by weight crude furfural product is normally collected in tank 64 during this step.

When tank 64 is filled with crude furfural of the desired concentration, the feed to column 54 is stopped by closing a valve (not shown) in line 52. At this point the bottom liquids in line 44 of column 16 are redirected via lines 46, 18 back to adsorption column 14 for simultaneous passage thereof with the dilute stream entering the system through line 18. In addition, the collected bottoms within tank 56 may also be recycled back for readsorption through lines 98, 104, 46 and 18, or be passed out of the system through lines 98, 100 and 102.

The next step involves the transfer of the crude furfural product within tank 64 to tank 56 via line 110, whereupon the crude furfural is redistilled in column 54. In this connection the crude furfural is recycled through lines 98, 100 and 106 and is vaporized using indirect steam from reboiler 108 as was the case in the first distillation procedure. In this instance however, a vacuum is drawn using source 62 through line 78, decanter 60, and lines 76 and 70. This vacuum-assisted distillation facilitates recovery of furfural as approximately 99% by weight purified product, since direct distillation would require higher temperature than 212° F and degrade the furfural. The furfural in water vapor passes out of column 54 through line 70 and is condensed in condenser 72. The condensate then passes via line 76 to decanter 60 wherein the saturated furfural in water solution is initially collected by overflowing as depicted by arrow 114 into overflow section 86 of the decanter. It then passes via line 92 to collection tank 64. A fraction of the initially received condensates of saturated water in furfural is also returned to the top of column 54 through lines 94, 96. As the saturated water in furfural solution begins to collect in decanter 60 and approaches the desired concentration (e.g., about 99% by weight pure), the vacuum pressure at the top of column 54 will drop. At this point the heavier water in furfural solution will be allowed to overflow as illustrated by arrow 114 into section 86 of decanter 60 and ultimately through line 92 to tank 64. Once the vacuum pressure stabilizes at approximately 100 mm. of mercury at the top of column 54 at a temperature of about 212° F, the water in the system will have been essentially removed and pure furfural product (approximately 99% by weight) can be directed through line 94 into drum loading apparatus 66.

After the furfural has been removed, the bottoms in line 44 from fractionation column 16 are redirected back through lines 46, 52 and 68 to vessel 56. The vacuum source 62 is then deactivated and crude furfural production as described above is restarted in the fractionator.

Thus, it will be seen that the present embodiment is capable of producing concentrated furfural on a continuous basis by providing a single second stage fractionator capable of doing the work of two or more such units in conventional processes.

EXAMPLE I

A stream of sulfite process waste condensate comprising condensed digester relief and blow gases, as well as the condensates derived from the evaporation of spent pulping liquor, is treated by the methods described above in connection with FIG. 1. The two carbon columns each contain 80,000 pounds of activated carbon and are sized for adsorbing furfural from the dilute waste condensate and recycle streams as desired for approximately 120 hours. The dilute condensate feed is cooled prior to adsorption and is analyzed to contain the following:

TABLE 1

| Constituents | % By Weight | Feed Rate (lb/hr) |
| --- | --- | --- |
| methanol | 0.13 | 124 |
| furfural | 0.07 | 72 |
| acetic acid | 0.61 | 602 |
| sulfur dioxide | 0.01 | 10 |
| water | 99.18 | 97,892 |
| TOTAL | 100.00 | 98,700 |

After the 120 hour period the activated carbon contains approximately the following:

TABLE 2

| Constituents | Pounds |
| --- | --- |
| furfural | 8,640 |
| sulfur dioxide | 1,200 |
| water | 70,160 |
| TOTAL | 80,000 |

The clarified feed leaving the adsorption carbon column is primarily water but also contains the acetic acid and methanol fraction from the original feed. This aqueous clarified feed can optionally be treated for the removal of acetic acid and methanol or be reused as desired.

During the adsorption stage described above, the remaining column (which is loaded with furfural) is reactivated by passing vaporized methanol at approximately 3.768 lb/hr for a total of seven hours, three hours downflowing through the carbon and four upflowing therethrough. During the upflow period, condensed methanol is recycled back to the top of the adsorption column with a fraction thereof being fed to the series-coupled fractionation column where the methanol is refluxed and either recycled back to the adsorption column in vaporized form or to a storage system. At the same time, the adsorption column underflow which includes the desorbed furfural is directed to the series-related fractionation column where it is separated from the methanol. The regeneration procedure is continued until only methanol is being removed from the top and bottom of the column being regenerated at approximately 1,884 lb/hr each.

The next step involves steam purging of the adsorption column to remove the methanol. This can be accomplished by using direct steam, but in continuous operations preferably is effected by utilizing the aqueous effluent from the second stage furfural recovery fractionation column 54 via lines 98, 104, 46, 47, and 42 which is vaporized by using indirect steam from reboiler 24.

The partially concentrated furfural crude leaving the first stage fractionator ultimately passes through line 52 and passes to second stage fractionator for the production of the 92% by weight furfural crude. However, the entire 80,000 lb of aqueous material initially desorbed from the activated carbon is preferably recycled back through the adsorption column with the continuing flow of dilute feed. Thereafter by ratio control half of the 80,000 lb of material per 120 hours is fed into the furfural recovery system. The partially condensed furfural directed to the second stage fractionator is analyzed to contain:

TABLE 3

| Constituents | Pounds | % By Weight |
| --- | --- | --- |
| furfural | 8,640 | 21.5 |
| polymerized material | 1,200 | 3.0 |
| water | 30,160 | 75.4 |
| TOTAL | 40,000 | 100.0 |

The furfural recovery system is designed to recover in the first stage 92% by weight furfural crude at the rate of approximately 9,391 lb in 60 hours. The remaining liquid, approximately 30,609 lb, leaves the bottom of the furfural fractionation column for recycling back to the adsorption column. Then for the remaining 60 hours of the 120 hours cycle, about 9,391 lb of 92% by weight crude is directed from tank 64 back to fractionation column 54 whereupon this 92% by weight crude is concentrated until eventually about 8,727 lb of 99% by weight furfural product is produced.

Thus, the same second stage fractionator is operable to alternately produce a 92% by weight crude furfural product and the finished, approximately 99% by weight product. This dual use is made possible by virtue of the use of an adsorption column capable of simultaneously handling the dilute feed stream and the recycled portion of the partially concentrated furfural from the second stage fractionator.

The remaining embodiments disclosed herein are in many respects identical with that of FIG. 1. Specifically, adsorption columns 14 and 14r and related apparatus are identical in each of the following embodiments, and accordingly this apparatus is not specifically depicted. Moreover, where applicable reference numerals used in connection with FIG. 1 will be retained but will include a lower case letter (a, b, or c) to denote the respective elements of FIGS. 2, 3, and 4. Thus, the description of the separate embodiments where identical with FIG. 1 will not be repeated hereinafter but can be determined from the parallel discussion given in connection with FIG. 1. Of course, the differences in apparatus and operation in each of the remaining figures will be fully explained.

FIG. 2 EMBODIMENT

Figure 2:
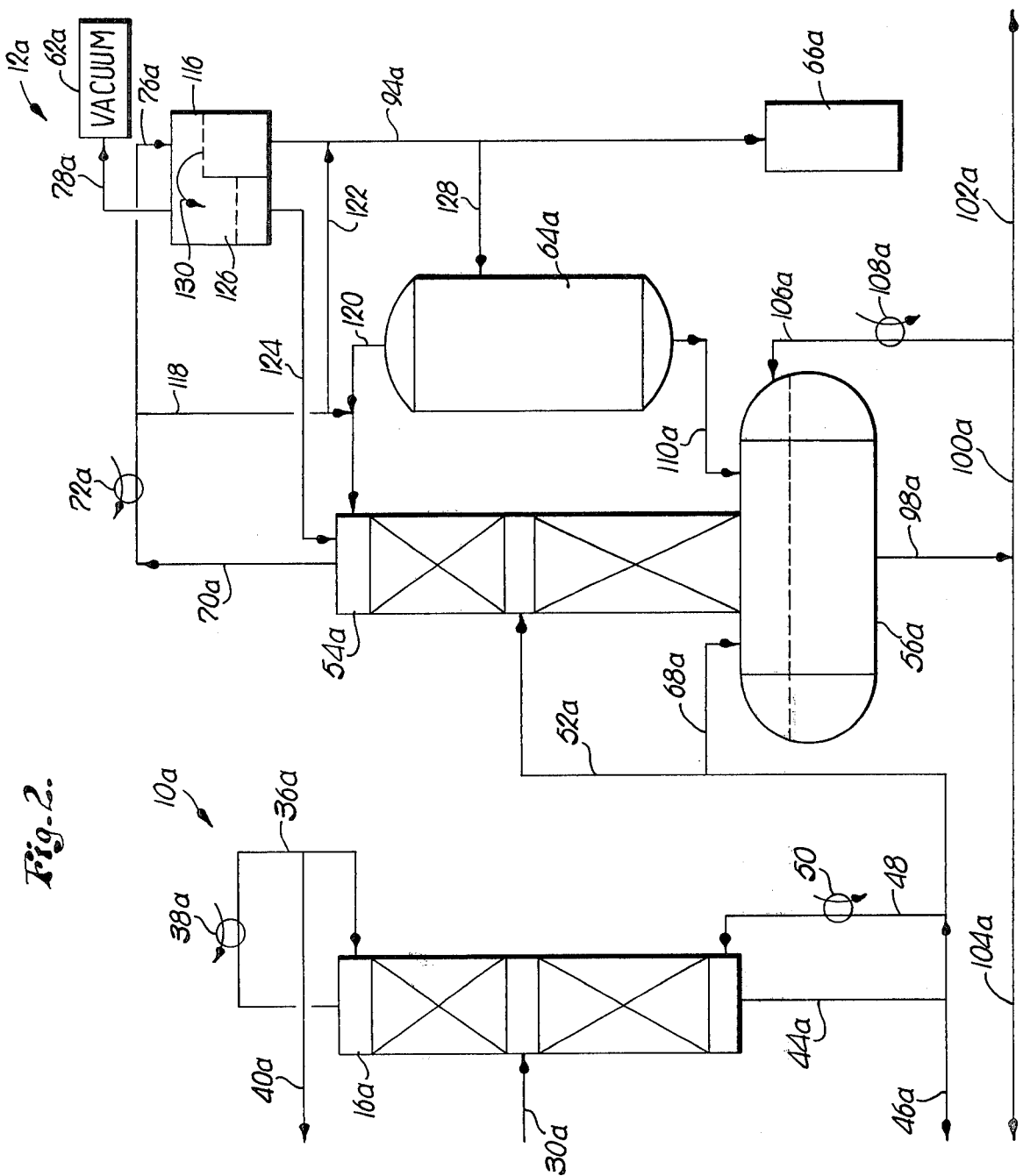
FIG. 2 is a fragmentary schematic representation of apparatus similar to that depicted in FIG. 1, but shown with the use of only a single decanter.

The embodiment disclosed in FIG. 2 includes an adsorption and concentration stage 10a and serially-related furfural recovery stage 12a. Stage 10a is identical in all respects with stage 10 of FIG. 1, and thus, the description of the apparatus and operation thereof will not be repeated. On the other hand, stage 12a differs from stage 12 of FIG. 1 only in the provision of a single decanter 116 as opposed to two decanters 58 and 60 in FIG. 1. In addition, a line 118 is connected between line 70a and a line 120 which extends from tank 64a to the top of column 54a. A tapoff line 122 extends between line 118 and line 94a as illustrated. A recycle line 124 extends between the overflow section 126 of decanter 116 and the top of column 54a. Finally, a line 128 extends between line 94a and tank 64a as depicted.

The operation of the FIG. 2 apparatus is identical ith that of FIG. 1 with respect to the initial stage 10a. During the initial fractionation procedure in stage 12a, the overhead from column 54a is condensed in condenser 72a and passes via line 76a to decanter 116. The saturated furfural in water solution collected within decanter 116 overflows as illustrated by arrow 130 into section 126 of decanter 116, and is recycled to the top of column 54a through line 124. The saturated water in furfural solution passes through lines 94a and 128 to tank 64a. This solution by gravity displaces the saturated furfural in water solution within tank 64a and forces it out the top of the latter through line 120 to the top of column 54a for further concentration.

When the desired concentration of crude furfural is collected within tank 64a (approximately 92% by weight), flow of partially concentrated furfural through line 52a to column 54a is stopped, and this stream is diverted back to the activated carbon adsorption zone for further adsorption and concentration of the furfural content thereof.

Simultaneously with this rediversion and further concentration, the crude furfural within tank 64a is passed by way of line 110a to tank 56a at the bottom of column 54a. Redistillation of the crude furfural is then commenced with indirect steam provided through reboilder 108a. This distillation is vacuum-assisted by provision of vacuum source 62a and is operable to distill and produce a highly concentrated furfural solution. In this regard, during initial stages of the final purification step, the condensed furfural-water vapor is recycled through lines 70a, 118 and 120 back to the top of column 54a and also is collected through lines 70a, 118a, 122, 94a and 128 back to tank 64. The remaining final vacuum purification procedure is exactly as described in FIG. 1 and serves to produce the highly concentrated furfural product which passes through line 94a to drum-loading apparatus 66a.

FIGURE 3 EMBODIMENT

The embodiment illustrated in FIG. 3 is basically the same as that depicted in FIG. 1 and includes an adsorption and concentration stage 10b and a final concentration and recovery stage 12b. Stage 10b includes a pair of parallel activated carbon columns, each containing approximately 80,000 lb. of activated carbon, along with the other apparatus illustrated in FIG. 1. In this embodiment, however, the dilute condensate feed line may be attached to the top of the columns, with the clarified feed recovery lines being connected to the bottom thereof.

This embodiment is particularly adapted for the production of concentrated furfural, but employs steam as the activated carbon desorbing agent. For this purpose, the apparatus is somewhat modified as set forth hereinafter.

First, a line 132 is interconnected between loop recycle line 38b and the mid-portion of fractionator 54b. On the other hand, a line 134 is connected to line 46b and extends to tank 56b for the delivery of the fractionator bottoms to tank 56b. In this instance, line 40b connected to loop line 38b is provided for recycling the column 16b overheads back for readsorption as necessary.

In operation, the adsorption step is identical with that described in connection with FIG. 1 and serves to load one of the parallel carbon columns of the adsorption zone. During regeneration, however, steam is directed to the regeneration lines connected to the appropriate regenerating column for removing the adsorbed fufural therefrom. In this regard, the steam may be direct or, more preferably, generated indirectly through the steam-fired reboiler interposed within the regeneration lines for the columns (see FIG. 1).

This steam regeneration has the effect of producing condensed quantities of aqueous, somewhat concentrated furfural which are directed via line 30b to column 16b. Conventional fractionation procedures within column 16*b* have the effect of producing an overhead in line 38*b* which comprises furfural and water. This overhead after recycling is directed through line 132*b* to second stage fractionator 54*b*. On the other hand, the bottoms in line 44*b* are recycled through line 48*b* and reboiler 50*b*, and are recycled back to the adsorption column through lines 46*b*. During the regeneration procedure, line 134 is normally closed and the fractionator overhead provides the sole supply of furfural to column 54*b*.

It will be appreciated that the piping changes made in connection with this embodiment stem from the use of steam as opposed to alcohol as the regenerating agent. That is, the alcohol employed in the FIG. 1 embodiment prevents the furfural from leaving as an overhead from the carbon columns and fractionator 16*b* since such alcohol breaks up the water-furfural azeotropes and renders the furfural relatively non-volatile. On the other hand, when stem is used as the regenerating agent, the probability of furfural exiting as overhead furfural-water azeotrope is enhanced.

The furfural recovery stage 12*b* in FIG. 3 is identical in every respect with that described in FIG. 1. Accordingly, a discussion of the operation of this stage will not be repeated herein but can be determined from the FIG. 1 discussion.

EXAMPLE II

The identical sulfite process waste condensates used in Example I are cooled and passed through 80,000 pounds of of activated carbon in an activated carbon column as described for approximately 120 hours. The adsorption results are identical to those described in Example I. In this instance the carbon is reactivated by passing steam into the bottom of the carbon column at 2,120 lb/hr. Direct steam is used for the first hour, and then the liquid from the bottom of the first stage regenerating fractionation column is vaporized using indirect steam. The condensed vapor from the top of the regenerating carbon column is initially recycled back into the top thereof and thereafter is combined with the liquid from its bottom section and fed into the first stage fractionation column. This feed contains:

TABLE 4

| Constituents | Pounds | % By Weight |
|---|---|---|
| furfural | 8,640 | 10.5 |
| sulfur dioxide | 1,200 | 1.5 |
| water | 72,280 | 88.0 |
| TOTAL | 82,120 | 100.0 |

The condensed overhead vapor is recycled back to the top section of this regeneration column as necessary, and then fed into the fufural recovery system at an eventual composition of approximately 30% by weight fufural and 70% by water and a flow rate of 28,800 pounds in 60 hours. The liquid from the regeneration column bottom is first recycled back through the adsorbing carbon column or discharged back to the mills recovery system at 53,320 pounds in 60 hours. The sulfur dioxide throughout the process polymerizes and forms nonvolatile sulfur components, which are eventually removed in the recovery system of the mill.

In the second stage fractionation column the furfural-water vapor overhead is condensed, and the condensate separates into two phases in the first decanter. The water in furfural phase contains 92% by weight furfural, and is collected in tank 64*b*. The furfural in water phase overflows back to the top of the recovery fractionation column through line 88*b*. 8.460 pounds of the water in furfural crude is recovered in the 60 hour period in tank 64*b*. Water removed from the bottom of the second stage fractionator 54*b* is discharged for reuse in the mill at the rate of 20,160 pounds in 60 hours.

At this time the furfural delivery to column 54*b* is terminated, and the column is placed on total reflux (nothing going into the recovery fractionation column). The crude furfural is thereafter recovered in the manner described in FIG. 1 and 8.727 pounds of 99% by weight furfural product is taken overhead and collected.

FIGURE 4 EMBODIMENT

The FIG. 4 embodiment broadly includes an adsorption concentration stage 10*c* and a series coupled concentration and recovery stage 12*c*. The overall apparatus is especially designed for the recovery of acetic acid from sulfite pulpmaking waste condensates. In one commercial embodiment, it is capable of producing glacial acetic acid from a 0.5% by weight acetic acid pulp mill effluent.

Again, stage 10*c* of FIG. 4 is identical in all respects to stage 10 of FIG. 1. However, in this case stage 12*c* is somewhat modified by virtue of the fact that acetic acid and water do not separate into two liquid phases which can be easily decanted. In particular, stage 12*c* includes a first reflux vessel 140 which is connected to line 74*c* as illustrated, along with a secondary reflux vessel 142 connected to line 76*c*. In addition, a line 144 extends from line 88*c* connected to vessel 140 and is ultimately attached to line 40*c* for reuse or disposal of methanol regenerating agent. In all other respects stage 12*c* is identical with stage 12 of FIG. 1.

In operation, steam and/or methanol can be used to regenerate the activated carbon from the column being regenerated in stage 10*c*. Acetic acid will be in the bottoms from the carbon columns as well as fractionator 16*c*, since it is less volatile than water. The acetic acid bottoms in line 44*c* are initially recycled through line 48*c* and reboiler 50*c* and are thereafter recycled through line 46*c* to the adsorbing carbon column for readsorption thereon. The overhead from column 16*c* is handled in the manner described in connection with FIG. 1 with the methanol exiting through line 40*c* for resue or storage. Subsequent to the initial recycling of the acetic acid, the acetic acid is directed through line 52*c* to second stage fractionator 54*c*. In this instance since the acetic acid is less volatile than water, the concentrated acetic acid will be collected in tank 56*c* instead of tank 64*c* as was the case with furfrl recovery. Water and furfural are removed as overhead vapor from column 54*c* via line 70*c*. The vaporized furfural and water are condensed in exchanger 72*c* and pass through line 74*c* into vessel 140. These materials ultimately pass through line 144*c* for disposal or further purification.

Once the acetic acid reaches a desired concentration in tank 56*c*, the feed through line 52*c* is terminated and diverted back to the adsorbing column through line 46*c*. At this point, the water and acetic acid within tank 56*c* are subjected to a further fractionation step, resulting in a vapor overhead through line 70*c* which is condensed in exchanger 72*c*. This condensate is directed through line 76*c*, vessel 142 and lines 94*c*, 96*c* and 146 to intermediate storage tank 64*c*. When the acetic acid is sufficiently concentrated and comes overhead, it is removed through line 94*c* to drum-loading apparatus 66*c*. Any polymerized and/or non-volatile material is removed through line 102c and can be recycled back to the evaporator system of the mill.

The stored intermediate concentrated acetic acid liquid is then discharged from tank 64c through line 110c to tank 56c. The feed through line 52c is once again started and the next recovery cycle begins.

EXAMPLE 3

The same sulfite process waste condensates used in Example I is cooled and passed through 80,000 pounds of activated carbon in the adsorbing activated carbon column for approximately 12 hours. This activated carbon then contains:

TABLE 5

| Constituents | Pounds |
|---|---|
| furfural | 864 |
| acetic acid | 7,224 |
| sulfur dioxide | 120 |
| water | 71,792 |
| TOTAL | 80,000 |

This carbon was regenerated using methanol in a manner exactly as described in FIG. 1.

During the regeneration cycle, the sulfur dioxide reacts with some furfural, acetic acid and methanol to form polymerized material and sulfur compounds which are no longer volatile. This material leaves the bottom of the first stage fractionation column with the other relatively less volatile materials as:

TABLE 6

| Constituents | Pounds | % By Weight |
|---|---|---|
| furfural | 864 | 1.08 |
| acetic acid | 7,224 | 9.03 |
| polymerized material | 120 | 0.15 |
| water | 71,792 | 89.74 |
| TOTAL | 80,000 | 100.00 |

This liquid is recycled and directed to the second stage fractionator in the manner described in Example I. In this instance however, eventually 26,700 pounds of liquid per 12 hours are fed as column bottoms into the acetic acid recovery system. This liquid is analysed to contain:

TABLE 7

| Constituents | Pounds | % By Weight |
|---|---|---|
| furfural | 864 | 3.2 |
| acetic acid | 7,224 | 27.1 |
| polymerized material | 120 | 0.4 |
| water | 18,492 | 69.3 |
| TOTAL | 26,700 | 100.00 |

In preferred forms about two-thirds of the liquid recovered as bottoms is recycled back to the adsorbing column.

During the first 6 hour period of each 12-hour cycle the 18,492 and 864 pounds of water and fufural respectively are removed as overhead from the second stage fractionation column. Then during the second 6 hour period while the feed is stopped to the second fractionator, intermediate water-acetic acid solution is collected in tank 64c, and 72,224 pounds of glacial acetic acid is made and collected as overhead from column 54c with or without the vacuum system operating. The polymerized material is tapped off the bottom of the recovery fractionation column at the rate of 120 pounds every 12 hours, and it is either burned or sold.

After the product has been made and the polymerized material removed, the feed is restarted into the second fractionation column and the intermediate water-acetic acid is discharged from tank 64c to tank 56c, and water and furfural are once again removed at the rate of 18,492 and 864 pounds in a 6 hour period. This permits continuous running of the recycling stage during the 12 hour adsorption stage.

What is claimed as new and desired to be secured by Letters Patent is:

1. A method of continuously handling a dilute stream containing an adsorbable chemical which is continuously fed to a recovery system, and of recovering a highly purified and concentrated stream of the adsorbable chemical, said method comprising the steps of:

continuously directing said dilute stream to an adsorption zone having a plurality of adsorption columns each containing adsorption media;

continuously passing said dilute stream through one of said columns and adsorbing at least a fraction of said chemical on said media therein, thereafter diverting said dilute stream to another of said columns, and continuously passing said dilute stream therethrough for adsorption of at least a fraction of said chemical on the media within said other column;

desorbing said adsorbed chemical on the media within said one column by passing a regenerating agent through the latter during the diversion of said dilute stream to said other column whereby said one column is again capable of receiving said dilute stream and adsorbing said chemical therefrom, and producing a partially concentrated stream containing said chemical which is more concentrated than said dilute stream;

continuously directing at least a fraction of said partially concentrated stream to a second concentration zone which includes concentration apparatus usable on a batch basis, and continuously concentrating said directed fraction of the partially concentrated stream to a desired level in the second concentration zone to thereby produce a further concentrated stream of said chemical and a bottoms fraction;

collecting said bottoms fraction and recycling the same back to said adsorption zone for passage therethrough simultaneously with said dilute stream in order to readsorb any of said chemical within said bottoms fraction on said adsorption media;

continuously collecting said further concentrated stream of said chemical in a holding zone;

stopping the delivery of said partially concentrated stream for a sufficient period of time to permit batch reconcentration in the concentration apparatus of said second concentration zone of at least a part of the further concentrated stream of said chemical held in said holding zone, and redirecting said partially concentrated stream back to said first concentration zone for maintaining the continuity of said method without storage or disposal of said partially concentrated stream;

passing said redirected, partially concentrated stream through said absorption zone simultaneously with said continuous dilute stream, with consequent readsorption of said chemical from the redirected stream onto said adsorption media;

conveying at least a part of said chemical held in said holding zone back to the concentration apparatus of the second concentration zone, after said stoppage and redirection of said partially concentrated stream;

producing a finally concentrated stream of said chemical by a batch concentration of the conveyed part of said further concentrated stream in the batch concentration apparatus of the second concentration zone during said redirection and passage of said partially concentrated stream through said adsorption zone; and recovering the finally concentrated stream of said chemical as the latter is produced by said batch concentration.

2. The method of claim 1 wherein said first concentration zone includes a first-stage fractionation zone, and said production of said partially concentrated stream includes the step of fractionally distilling the desorbed chemical from the adsorption zone in the first fractionation zone.

3. The method of claim 1 wherein said second concentration zone includes a second-stage fractionation zone, and said production of said further concentrated stream includes the step of fractionally distilling the directed part of said partially concentrated stream in the second-stage fractionation zone.

4. The method of claim 3 wherein the production of said further concentrated stream includes the steps of condensing and decanting the distillate from said second-stage fractionation zone.

5. The method of claim 3 wherein the production of said finally concentrated stream includes the step of a batch redistillation of the conveyed part of said further concentrated stream in said second-stage fractionation zone.

6. The method of claim 1 wherein said chemical is selected from the group consisting of furfural and acetic acid.

7. The method of claim 1 wherein said dilute stream comprises sulfite pulp-making waste condensates which contain quantities of furfural, acetic acid, methanol and sulfur dioxide.

8. The method of claim 1 wherein said adsorption media is activated carbon.

9. The method of claim 8 wherein said regeneration agent is selected from the group consisting of methanol and steam.

10. The method of claim 1 wherein said regeneration agent is selected from the group consisting of the lower alcohols, acetone and moisture.

11. The method of claim 1 including the step of purging said adsorption media of said regeneration agent subsequent to said desorbing step.

12. The method of claim 1 wherein said regeneration agent is sequentially passed in opposite directions through said adsorption media.

* * * * *